United States Patent
Chaudhuri et al.

(10) Patent No.: US 7,511,164 B2
(45) Date of Patent: Mar. 31, 2009

(54) CREATINE-FATTY ACIDS

(75) Inventors: Shan Chaudhuri, Mississauga (CA); Joseph MacDougall, Mississauga (CA); Jason Peters, Mississauga (CA); James Ramsbottom, Mississauga (CA)

(73) Assignee: Multi Formulations Ltd, Mississauga, Ontario (CA)

( * ) Notice: Subject to any disclaimer, the term of this patent is extended or adjusted under 35 U.S.C. 154(b) by 116 days.

(21) Appl. No.: 11/856,374

(22) Filed: Sep. 17, 2007

(65) Prior Publication Data

US 2008/0200723 A1 Aug. 21, 2008

Related U.S. Application Data

(63) Continuation of application No. 11/676,623, filed on Feb. 20, 2007, now Pat. No. 7,314,945.

(51) Int. Cl.
*C07C 51/00* (2006.01)
(52) U.S. Cl. ..................................... 554/152
(58) Field of Classification Search .................. None
See application file for complete search history.

(56) References Cited

U.S. PATENT DOCUMENTS

| 3,024,272 | A | 3/1962 | Hyson et al. |
| 5,994,581 | A | 11/1999 | Fang |
| 2004/0023889 | A1 | 2/2004 | Gardiner et al. |

FOREIGN PATENT DOCUMENTS

| CA | 1022849 | | 12/1977 |
| CA | 2577439 | A1 | 5/2007 |
| EP | 0339498 | | 11/1989 |
| WO | 03/099806 | A1 | 12/2003 |
| WO | 03/101402 | A2 | 12/2003 |
| WO | 2006/081682 | A1 | 8/2006 |

OTHER PUBLICATIONS

Harris RC, et al. Elevation of creatine in resting and exercised muscle of normal subjects by creatine supplementation. Clin Sci (Lond). Sep. 1992;83(3):367-74.
Greenhaff PL, et al. Effect of oral creatine supplementation on skeletal muscle phosphocreatine resynthesis. Am J Physiol. May 1994;266(5 Pt 1):E725-30.
Greenhaff PL, et al. Influence of oral creatine supplementation of muscle torque during repeated bouts of maximal voluntary exercise in man. Clin Sci (Lond). May 1993;84(5):565-71.
Olsen S, et al. Creatine supplementation augments the increase in satellite cell and myonuclei number in human skeletal muscle induced by strength training. J Physiol. Jun. 2006;573(Pt 2):525-34.
Zammit PS, et al. The Skeletal Muscle Satellite Cell: The Stem Cell That Came In From the Cold. J Histochem Cytochem. Aug. 2006; 54(11):1177-91.
Sartorelli V, et al. Molecular and cellular determinants of skeletal muscle atropy and hypertropy. Sci STKE. 2004 Jul.;2004(244):re11.
Williams MH, et al. Creatine supplementation and exercise performance: an update. J Am Coll Nutr. Jun. 1998;17 (3):216-34.
Dox AW, et al. Esterification of creatine. J Biol Chem. 1922;67:671-73.
PCT/CA2007/000257 International Search Report, International Filing Date: Feb. 20, 2007, Applicant: Multi Formulations Ltd. et al., date mailed: Jul. 18, 2007.
PCT International Search Report, PCT/CA2007/001640, International Filing date: Sep. 14, 2007, Applicant: Multi Formulations Ltd. et al.
PCT International Search Report, PCT/CA2007/000810, International Filing date: May 10, 2007, Applicant: Multi Formulations Ltd. et al.

*Primary Examiner*—Deborah D. Carr
(74) *Attorney, Agent, or Firm*—Torys LLP

(57) ABSTRACT

The present invention describes compounds produced from a creatine molecule and a fatty acid molecule. The compounds being in the form of creatine-fatty acid compounds being bound by an anhydride linkage, or mixtures thereof made by reacting creatine or derivatives thereof with an appropriate fatty acid previously reacted with a thionyl halide. The administration of such molecules provides supplemental creatine with enhanced bioavailability and the additional benefits conferred by the specific fatty acid.

6 Claims, No Drawings

CREATINE-FATTY ACIDS

RELATED APPLICATION

This application is a continuation of the applicant's U.S. application Ser. No. 11/676,623, filed Feb. 20, 2007 now U.S. Pat. No. 7,314,945 and claims benefit of priority thereto.

FIELD OF THE INVENTION

The present invention relates to structures and synthesis of creatine-fatty acid compounds bound via an anhydride linkage. Another aspect of the present invention relates to a compound comprising a creatine molecule bound to a fatty acid, wherein the fatty acid is preferably a saturated fatty acid and bound to the creatine via an anhydride linkage.

BACKGROUND OF THE INVENTION

Creatine is a naturally occurring amino acid derived from the amino acids glycine, arginine, and methionine. Although it is found in meat and fish, it is also synthesized by humans. Creatine is predominantly used as a fuel source in muscle. About 65% of creatine is stored in the musculature of mammals as phosphocreatine (creatine bound to a phosphate molecule).

Muscular contractions are fueled by the dephosphorylation of adenosine triphosphate (ATP) to produce adenosine diphosphate (ADP). In the absence of a mechanism to replenish ATP stores, the supply of ATP would be totally consumed in 1-2 seconds. Phosphocreatine serves as a major source of phosphate from which ADP is regenerated to ATP. Within six seconds following the commencement of exercise, muscular concentrations of phosphocreatine drop by almost 50%. Creatine supplementation has been shown to increase the concentration of creatine in the muscle (Harris R C, Soderlund K, Hultman E. Elevation of creatine in resting and exercised muscle of normal subjects by creatine supplementation. Clin Sci (Lond). 1992 September; 83(3):367-74) and further, the supplementation enables an increase in the resynthesis of phosphocreatine (Greenhaff P L, Bodin K, Soderlund K, Hultman E. Effect of oral creatine supplementation on skeletal muscle phosphocreatine resynthesis. Am J Physiol. 1994 May; 266(5 Pt 1):E725-30) leading to a rapid replenishment of ATP within the first two minutes following the commencement of exercise. Through this mechanism, creatine is able to improve strength and reduce fatigue (Greenhaff P L, Casey A, Short A H, Harris R, Soderlund K, Hultman E. Influence of oral creatine supplementation of muscle torque during repeated bouts of maximal voluntary exercise in man. Clin Sci (Lond). 1993 May; 84(5):565-71).

The beneficial effects of creatine supplementation with regard to skeletal muscle are apparently not restricted to the role of creatine in energy metabolism. It has been shown that creatine supplementation in combination with strength training results in specific, measurable physiological changes in skeletal muscle compared to strength training alone. For example, creatine supplementation amplifies the strength training-induced increase of human skeletal satellite cells as well as the number of myonuclei in human skeletal muscle fibres (Olsen S, Aagaard P, Kadi F, Tufekovic G, Verney J, Olesen J L, Suetta C, Kjaer M. Creatine supplementation augments the increase in satellite cell and myonuclei number in human skeletal muscle induced by strength training. J Physiol. 2006 Jun. 1; 573(Pt 2):525-34). Satellite cells are the stem cells of adult muscle. They are normally maintained in a quiescent state and become activated to fulfill roles of routine maintenance, repair and hypertrophy (Zammit P S, Partridge T A, Yablonka-Reuveni Z. The Skeletal Muscle Satellite Cell: The Stem Cell That Came In From the Cold. J Histochem Cytochem. 2006 Aug. 9). 'True' muscle hypertrophy can be defined as "as an increase in fiber diameter without an apparent increase in the number of muscle fibers, accompanied by enhanced protein synthesis and augmented contractile force" (Sartorelli V, Fulco M. Molecular and cellular determinants of skeletal muscle atrophy and hypertrophy. Sci STKE. 2004 Jul. 27; 2004(244):re11). Postnatal muscle growth involves both myofiber hypertrophy and increased numbers of myonuclei—the source of which are satellite cells (Olsen S, Aagaard P, Kadi F, Tufekovic G, Verney J, Olesen J L, Suetta C, Kjaer M. Creatine supplementation augments the increase in satellite cell and myonuclei number in human skeletal muscle induced by strength training. J Physiol. 2006 Jun. 1; 573(Pt 2):525-34).

Although creatine is used predominantly in muscle cells and most of the total creatine pool is found in muscle, creatine is actually synthesized in the liver and pancreas. Thus, the musculature's creatine concentration is maintained by the uptake of creatine from the blood stream regardless of whether the source of creatine is endogenous, i.e. synthesized by the liver or pancreas, or dietary, i.e. natural food sources or supplemental sources. The creatine content of an average 70 kg male is approximately 120 g with about 2 g being excreted as creatinine per day (Williams M H, Branch J D. Creatine supplementation and exercise performance: an update. J Am Coll Nutr. 1998 June; 17(3):216-34). A typical omnivorous diet supplies approximately 1 g of creatine daily, while diets higher in meat and fish will supply more creatine. As a point of reference, a 500 g uncooked steak contains about 2 g of creatine which equates to more than two 8 oz. steaks per day. Since most studies examining creatine supplementation employ dosages ranging from 2-20 g per day it is unrealistic to significantly increase muscle creatine stores through merely food sources alone. Therefore, supplemental sources of creatine are an integral component of increasing, and subsequently maintaining supraphysiological, muscular creatine levels.

Creatine supplementation, thus results in positive physiological effects on skeletal muscle, such as: performance improvements during brief high-intensity anaerobic exercise, increased strength and enhanced muscle growth.

Creatine monohydrate is a commonly used supplement. Creatine monohydrate is soluble in water at a rate of 75 ml of water per gram of creatine. Ingestion of creatine monohydrate, therefore, requires large amounts of water to be co-ingested. Additionally, in aqueous solutions creatine is known to convert to creatinine via an irreversible, pH-dependent, non-enzymatic reaction. Aqueous and alkaline solutions contain an equilibrium mixture of creatine and creatinine. In acidic solutions, on the other hand, the formation of creatinine is complete. Creatinine is devoid of the ergogenic beneficial effects of creatine. It is therefore desirable to provide, for use in individuals, e.g. animals and humans, forms and derivatives of creatine with improved characteristics such as stability and solubility. Furthermore, it would be advantageous to do so in a manner that provides additional functionality as compared to creatine monohydrate alone.

The manufacture of hydrosoluble creatine salts with various organic acids have been described. U.S. Pat. No. 5,886,040, purports to describe a creatine pyruvate salt with enhanced palatability which is resistant to acid hydrolysis.

U.S. Pat. No. 5,973,199, purports to describe hydrosoluble organic salts of creatine as single combination of one mole of creatine monohydrate with one mole of the following organic acids: citrate, malate, fumarate and tartarate individually. The resultant salts described therein are claimed to be from 3 to 15 times more soluble, in aqueous solution, than creatine itself.

U.S. Pat. No. 6,166,249, purports to describe a creatine pyruvic acid salt that is highly stable and soluble. It is further purported that the pyruvate included in the salt may be useful to treat obesity, prevent the formation of free radicals and enhance long-term performance.

U.S. Pat. No. 6,211,407 purports to describe dicreatine and tricreatine citrates and a method of making the same. These dicreatine and tricreatine salts are claimed to be stable in acidic solutions, thus hampering the undesirable conversion of creatine to creatinine.

U.S. Pat. No. 6,838,562, purports to describe a process for the synthesis of mono, di, or tricreatine orotic acid, thioorotic acid, and dihydroorotic acid salts which are claimed to have increased oral absorption and bioavailability due to an inherent stability in aqueous solution. It is further claimed that the heterocyclic acid portion of the salt acts synergistically with creatine.

U.S. Pat. No. 7,109,373, incorporated herein in its entirety by reference, purports to describe creatine salts of dicarboxylic acids with enhanced aqueous solubility.

The above disclosed patents recite creatine salts, methods of synthesis of the salts, and uses thereof. However, nothing in any of the disclosed patents teaches, suggests or discloses a compound comprising a creatine molecule bound to a fatty acid.

In addition to salts, creatine esters have also been described. U.S. Pat. No. 6,897,334 describes method for producing creatine esters with lower alcohols i.e. one to four carbon atoms, using acid catalysts. It is stated that creatine esters are more soluble than creatine. It is further stated that the protection of the carboxylic acid moiety of the creatine molecule by ester-formation stabilizes the compound by preventing its conversion to creatinine. The creatine esters are said to be converted into creatine by esterases i.e. enzymes that cleave ester bonds, found in a variety of cells and biological fluids.

Fatty acids are carboxylic acids, often containing a long, unbranched chain of carbon atoms and are either saturated or unsaturated. Saturated fatty acids do not contain double bonds or other functional groups, but contain the maximum number of hydrogen atoms, with the exception of the carboxylic acid group. In contrast, unsaturated fatty acids contain one or more double bonds between adjacent carbon atoms, of the chains, in cis or trans configuration The human body can produce all but two of the fatty acids it requires, thus, essential fatty acids are fatty acids that must be obtained from food sources due to an inability of the body to synthesize them, yet are required for normal biological function. The essential fatty acids being linoleic acid and α-linolenic acid.

Examples of saturated fatty acids include, but are not limited to myristic or tetradecanoic acid, palmitic or hexadecanoic acid, stearic or octadecanoic acid, arachidic or eicosanoic acid, behenic or docosanoic acid, butyric or butanoic acid, caproic or hexanoic acid, caprylic or octanoic acid, capric or decanoic acid, and lauric or dodecanoic acid, wherein the aforementioned comprise from at least 4 carbons to 22 carbons in the chain.

Examples of unsaturated fatty acids include, but are not limited to oleic acid, linoleic acid, linolenic acid, arachidonic acid, palmitoleic acid, eicosapentaenoic acid, docosahexaenoic acid and erucic acid, wherein the aforementioned comprise from at least 4 carbons to 22 carbons in the chain.

Fatty acids are capable of undergoing chemical reactions common to carboxylic acids. Of particular relevance to the present invention are the formation of salts and the formation of esters. The majority of the above referenced patents are creatine salts. These salts, esterification via carboxylate reactivity, may essentially be formed, as disclosed in U.S. Pat. No. 7,109,373, through a relatively simple reaction by mixing a molar excess of creatine or derivative thereof with an aqueous dicarboxylic acid and heating from room temperature to about 50° C.

Alternatively, a creatine-fatty acid may be synthesized through ester formation. The formation of creatine esters has been described (Dox A W, Yoder L. Esterification of Creatine. J. Biol. Chem. 1922, 67, 671-673). These are typically formed by reacting creatine with an alcohol in the presence of an acid catalyst at temperatures from 35° C. to 50° C. as disclosed in U.S. Pat. No. 6,897,334.

While the above referenced creatine compounds have attempted to address issues such as stability and solubility in addition to, and in some cases, to add increased functionality as compared to creatine alone, no description has yet been made of any creatine-fatty acid compound, particularly that comprising a saturated fatty acid.

SUMMARY OF THE INVENTION

In the present invention, compounds are disclosed, where the compounds comprise a molecule of creatine bound to a fatty acid, via an anhydride linkage, and having a structure of Formula 1:

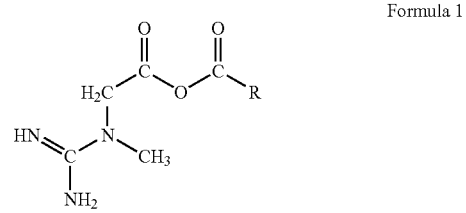

Formula 1 where:
  R is an alkyl group, preferably saturated, and containing from about 3 to a maximum of 21 carbons.

Another aspect of the invention comprises the use of a saturated fatty acid in the production of compounds disclosed herein.

A further aspect of the present invention comprises the use of an unsaturated fatty in the production of compounds disclosed herein.

DETAILED DESCRIPTION OF THE INVENTION

In the following description, for the purposes of explanation, numerous specific details are set forth in order to provide a thorough understanding of the present invention. It will be apparent, however, to one skilled in the art that the present invention may be practiced without these specific details.

The present invention relates to structures and synthesis of creatine-fatty acid compounds bound via an anhydride linkage. In addition, specific benefits are conferred by the particular fatty acid used to form the compounds in addition to, and separate from, the creatine substituent.

As used herein, the term 'fatty acid' includes both saturated, i.e. an alkane chain as known in the art, having no double bonds between carbons of the chain and having the maximum number of hydrogen atoms, and unsaturated, i.e. an alkene or alkyne chain, having at least one double or alternatively triple bond between carbons of the chain, respectively, and further terminating the chain in a carboxylic acid as is commonly known in the art, wherein the hydrocarbon chain is not less then four carbon atoms. Furthermore, essential fatty acids are herein understood to be included by the term 'fatty acid'.

As used herein, "creatine" refers to the chemical N-methyl-N-guanyl Glycine, (CAS Registry No. 57-00-1), also known as, (alpha-methyl guanido) acetic acid, N-(aminoiminomethyl)-N-glycine, Methylglycocyamine, Methylguanidoacetic Acid, or N-Methyl-N-guanylglycine. Additionally, as used herein, "creatine" also includes derivatives of creatine such as esters, and amides, and salts, as well as other derivatives, including derivatives having pharmacoproperties upon metabolism to an active form.

According to the present invention, the compounds disclosed herein comprise a creatine molecule bound to a fatty acid, wherein the fatty acid is preferably a saturated fatty acid. Furthermore, the creatine and fatty acid being bound by an anhydride linkage and having a structure according to Formula 1. The aforementioned compound being prepared according to the reaction as set forth for the purposes of the description in Scheme 1:

In alternative embodiments, of the present invention, the fatty acid of (2) is selected from the unsaturated fatty acid group comprising oleic acid, linoleic acid, linolenic acid, arachidonic acid, palmitoleic acid, eicosapentaenoic acid, docosahexaenoic acid, and erucic acid.

Furthermore, the thionyl halide of (3) is selected from the group consisting of fluorine, chlorine, bromine, and iodine, the preferred method using chlorine or bromine.

The above reaction proceeds under conditions of heat ranging between from about 35° C. to about 50° C. and stirring over a period from about 0.5 hours to about 2 hours during which time the gases sulfur dioxide and acidic gas, wherein the acidic gas species is dependent on the species of thionyl halide employed, are evolved. Preferably, the reaction proceeds at 45° C. for 1.5 hours.

Step 2 of Scheme 1 entails the neutralization of the carboxylic acid of the creatine portion through the addition of an inorganic base. The inorganic base is selected from the group comprising sodium hydroxide, potassium hydroxide, lithium hydroxide, ammonium hydroxide, sodium carbonate. Preferred inorganic bases for the purposes of the present invention are sodium hydroxide and potassium hydroxide.

Neutralization, as described above, is followed by the evaporation of water, resulting in the isolation of the corre-

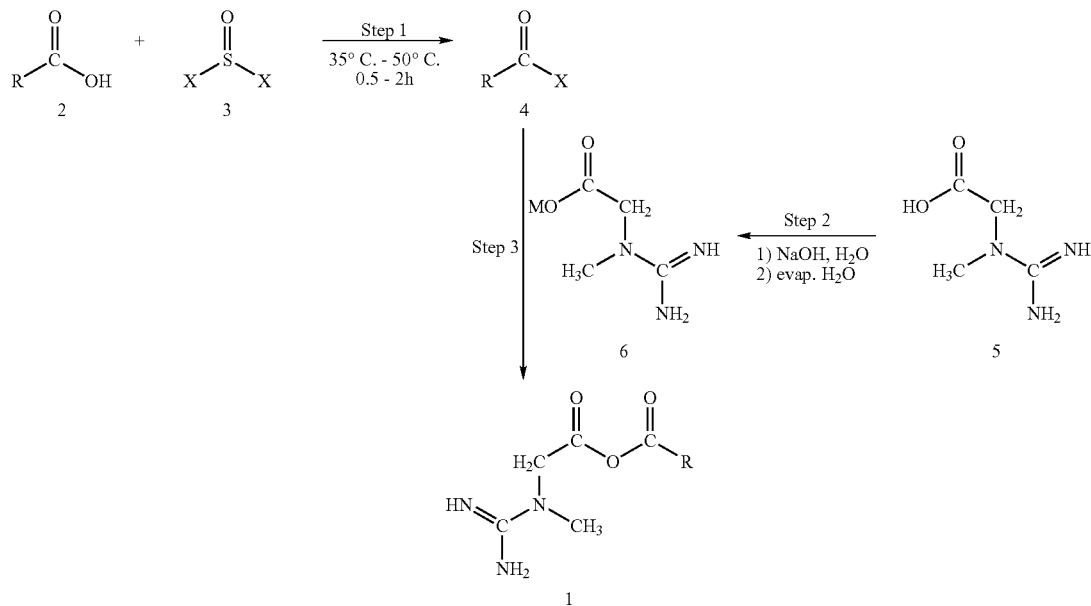

Scheme 1 where:
R = alkane or alkene (C = 3 to 21)
X = Cl, Br, F, or I
M = Na, K, Li, or NH4

With reference to Scheme 1, in Step 1 an acyl halide (4) is produced via reaction of a fatty acid (2) with a thionyl halide (3).

In various embodiments of the present invention, the fatty acid of (2) is selected from the saturated fatty acid group comprising butyric or butanoic acid, caproic or hexanoic acid, caprylic or octanoic acid, capric or decanoic acid, lauric or dodecanoic acid, myristic or tetradecanoic acid, palmitic or hexadecanoic acid, stearic or octadecanoic acid, arachidic or eicosanoic acid, and behenic or docosanoic acid.

sponding salt. For example, potassium hydroxide, when used as the inorganic base, results in the production of the potassium creatine salt.

Step 3 of Scheme 1 involves the drop wise addition of the prepared acyl halide (4) to the creatine salt (6) in a cooled flask and subsequent purification by two rounds of distillation to yield the desired anhydride compound (I), the anhydride compound being a creatine fatty acid compound of the present invention.

In various embodiments, according to aforementioned, using the saturated fatty acids, the following compounds are produced: butyric 2-(1-methylguanidino)acetic anhydride, hexanoic 2-(1-methylguanidino)acetic anhydride, 2-(1-methylguanidino)acetic octanoic anhydride, decanoic 2-(1-methylguanidino)acetic anhydride, 2-(1-methylguanidino)acetic tetradecanoic anhydride, 2-(1-methylguanidino)acetic palmitic anhydride, icosanoic 2-(1-methylguanidino)acetic anhydride, and docosanoic 2-(1-methylguanidino)acetic anhydride.

In additional embodiments, according to aforementioned, using the unsaturated fatty acids, the following compounds are produced: (Z)-hexadec-9-enoic 2-(1-methylguanidino) acetic anhydride, 2-(1-methylguanidino)acetic oleic anhydride, (Z)-docos-13-enoic 2(1-methylguanidino)acetic anhydride, 2-(1-methylguanidino)acetic (9Z,12Z)-octadeca-9,12-dienoic anhydride, 2-(1-methylguanidino)acetic (9Z,12Z,15Z)-octadeca-9,12,15-trienoic anhydride, 2-(1-methylguanidino)acetic (6Z,9Z,12Z)-octadeca-6,9,12-trienoic anhydride, (5Z,8Z,11Z,14Z)-icosa-5,8,11,14-tetraenoic 2(1-methylguanidino)acetic anhydride, (5Z,8Z,11Z,14Z,17Z)-icosa-5,8,11,14,17-pentaenoic 2(1-methylguanidino)acetic anhydride, 2(1-methylguanidino)acetic (8Z,11Z,14Z, 17Z,20Z)-tricosa-5,8,11,14,17,20-hexaenoic anhydride.

The following examples illustrate specific creatine-fatty acids and routes of synthesis thereof. One of skill in the art may envision various other combinations within the scope of the present invention, considering examples with reference to the specification herein provided.

EXAMPLE 1

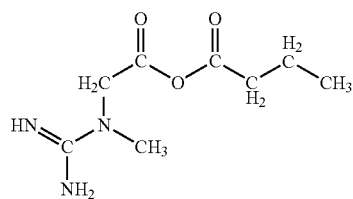

Butyric 2-(1-methylguanidino)acetic anhydride

In a dry 2-necked, round bottomed flask, equipped with a magnetic stirrer and fixed with a separatory funnel, containing 8.75 ml (120 mmol) of thionyl chloride, and a water condenser, is placed 9.05 ml (100 mmol) of butanoic acid. Addition of the thionyl chloride is completed with heating to about 40° C. over the course of about 30 minutes. When addition of the thionyl chloride is complete the mixture is heated and stirred for an additional 30 minutes. The water condenser is then replaced with a distillation side arm condenser and the crude mixture is distilled. The crude distillate in the receiving flask is then fractionally distilled to obtain the acyl chloride, butyryl chloride.

Separately, in a single-necked, round bottomed flask, equipped with a magnetic stirrer, 6.56 g (50 mmol) of creatine is dissolved in 500 ml of water. To this is added 55 ml of 1M sodium hydroxide with vigorous stirring, until heat production ceases. At this point the water is removed by evaporation to yield the carboxylate salt, sodium 2-(1-methylguanidino) acetate, shown below.

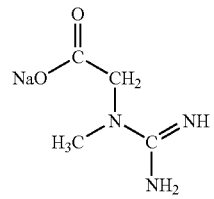

Finally, in a dry 2-necked, round bottomed flask, fixed with a separatory funnel, containing 6.39 g (60 mmol) of the prepared butyryl chloride, and side arm water condenser fixed with a dry receiving flask, is placed 12.08 g (66 mmol) of sodium 2-(1-methylguanidino)acetate. The round bottomed flask is placed in an ice bath and the butyryl chloride is added drop wise. After addition is completed the mixture is shaken and the ice bath is replaced by a heating mantle. The flask is then heated until no more solution is dropping into the receiving flask. This crude distillate is then further fractionally distilled to yield butyric 2-(1-methylguanidino)acetic anhydride.

EXAMPLE 2

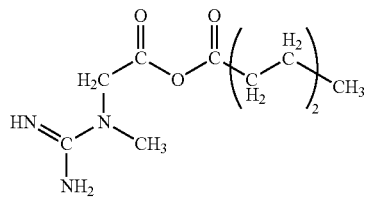

Hexanoic 2-(1-methylguanidino)acetic anhydride

In a dry 2-necked, round bottomed flask, equipped with a magnetic stirrer and fixed with a separatory funnel, containing 6.97 ml (90 mmol) of thionyl bromide, and a water condenser, is placed 5.68 ml (45 mmol) of hexanoic acid. Addition of the thionyl bromide is completed with heating to about 50° C. over the course of about 50 minutes. When addition of the thionyl bromide is complete the mixture is heated and stirred for an additional hour. The water condenser is then replaced with a distillation side arm condenser and the crude mixture is distilled. The crude distillate in the receiving flask is then fractionally distilled to obtain the acyl bromide, hexanoyl bromide.

Separately, in a single-necked, round bottomed flask, equipped with a magnetic stirrer, 6.56 g (50 mmol) of creatine is dissolved in 500 ml of water. To this is added 55 ml of 1M sodium hydroxide with vigorous stirring, until heat production ceases. At this point the water is removed by evaporation to yield the carboxylate salt, sodium 2-(1-methylguanidino) acetate, shown below.

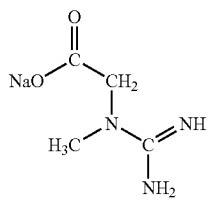

Finally, in a dry 2-necked, round bottomed flask, fixed with a separatory funnel, containing 10.81 g (60 mmol) of the prepared hexanoyl bromide, and side arm water condenser fixed with a dry receiving flask, is placed 13.18 g (72 mmol) of sodium 2-(1-methylguanidino)acetate. The round bottomed flask is placed in an ice bath and the hexanoyl bromide is added drop wise. After addition is completed the mixture is shaken and the ice bath is replaced by a heating mantle. The flask is then heated until no more solution is dropping into the receiving flask. This crude distillate is then further fractionally distilled to yield hexanoic 2-(1-methylguanidino)acetic anhydride.

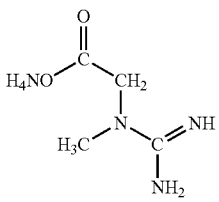

Finally, in a dry 2-necked, round bottomed flask, fixed with a separatory funnel, containing 15.31 g (70 mmol) of the prepared dodecanoyl chloride, and side arm water condenser fixed with a dry receiving flask, is placed 12.44 g (84 mmol) of ammonium 2-(1-methylguanidino)acetate. The round bottomed flask is placed in an ice bath and the dodecanoyl chloride is added drop wise. After addition is completed the mixture is shaken and the ice bath is replaced by a heating mantle. The flask is then heated until no more solution is dropping into the receiving flask. This crude distillate is then further fractionally distilled to yield dodecanoic 2-(1-methylguanidino)acetic anhydride.

EXAMPLE 3

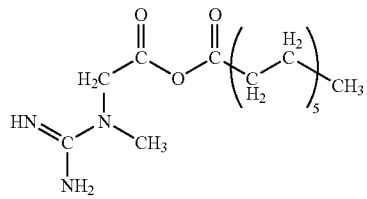

Dodecanoic 2-(1-methylguanidino)acetic anhydride

In a dry 2-necked, round bottomed flask, equipped with a magnetic stirrer and fixed with a separatory funnel, containing 5.85 ml (80 mmol) of thionyl chloride, and a water condenser, is placed 10.02 g (50 mmol) of dodecanoic acid. Addition of the thionyl chloride is completed with heating to about 45° C. over the course of about 40 minutes. When addition of the thionyl chloride is complete the mixture is heated and stirred for an additional 50 minutes. The water condenser is then replaced with a distillation side arm condenser and the crude mixture is distilled. The crude distillate in the receiving flask is then fractionally distilled to obtain the acyl chloride, dodecanoyl chloride.

Separately, in a single-necked, round bottomed flask, equipped with a magnetic stirrer, 7.87 g (60 mmol) of creatine is dissolved in 600 ml of water. To this is added 78 ml of 1M ammonium hydroxide with vigorous stirring, until heat production ceases. At this point the water is removed by evaporation to yield the carboxylate salt, ammonium 2-(1-methylguanidino)acetate, shown below.

EXAMPLE 4

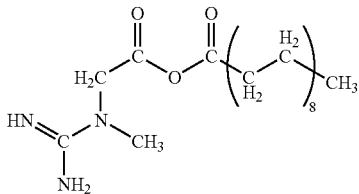

2-(1-methylguanidino)acetic stearic anhydride

In a dry 2-necked, round bottomed flask, equipped with a magnetic stirrer and fixed with a separatory funnel, containing 4.81 ml (66 mmol) of thionyl chloride, and a water condenser, is placed 15.65 g (55 mmol) of stearic acid. Addition of the thionyl chloride is completed with heating to about 45° C. over the course of about 40 minutes. When addition of the thionyl chloride is complete the mixture is heated and stirred for an additional 45 minutes. The water condenser is then replaced with a distillation side arm condenser and the crude mixture is distilled. The crude distillate in the receiving flask is then fractionally distilled to obtain the acyl chloride, stearoyl chloride.

Separately, in a single-necked, round bottomed flask, equipped with a magnetic stirrer, 7.87 g (60 mmol) of creatine is dissolved in 600 ml of water. To this is added 72 ml of 1M potassium hydroxide with vigorous stirring, until heat production ceases. At this point the water is removed by evaporation to yield the carboxylate salt, potassium 2-(1-methylguanidino)acetate, shown below.

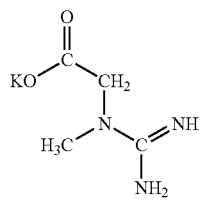

Finally, in a dry 2-necked, round bottomed flask, fixed with a separatory funnel, containing 21.27 g (70 mmol) of the prepared stearoyl chloride, and side arm water condenser fixed with a dry receiving flask, is placed 23.40 g (77 mmol) of potassium 2-(1-methylguanidino)acetate. The round bottomed flask is placed in an ice bath and the stearoyl chloride is added drop wise. After addition is completed the mixture is shaken and the ice bath is replaced by a heating mantle. The flask is then heated until no more solution is dropping into the receiving flask. This crude distillate is then further fractionally distilled to yield 2-(1-methylguanidino)acetic stearic anhydride.

EXAMPLE 5

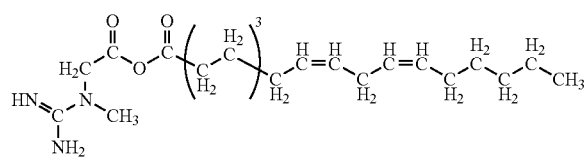

2-(1-methylguanidino)acetic (9Z,12Z)-octadeca-9, 12-dienoic anhydride

In a dry 2-necked, round bottomed flask, equipped with a magnetic stirrer and fixed with a separatory funnel, containing 9.35 ml (128 mmol) of thionyl chloride, and a water condenser, is placed 24.90 ml (80 mmol) of linoleic acid. Addition of the thionyl chloride is completed with heating to about 40° C. over the course of about 40 minutes. When addition of the thionyl chloride is complete the mixture is heated and stirred for an additional 50 minutes. The water condenser is then replaced with a distillation side arm condenser and the crude mixture is distilled. The crude distillate in the receiving flask is then fractionally distilled to obtain the acyl chloride, (9Z,12Z)-octadeca-9,12-dienoyl chloride.

Separately, in a single-necked, round bottomed flask, equipped with a magnetic stirrer, 7.87 g (60 mmol) of creatine is dissolved in 600 ml of water. To this is added 78 ml of 1M ammonium hydroxide with vigorous stirring, until heat production ceases. At this point the water is removed by evaporation to yield the carboxylate salt, ammonium 2-(1-methylguanidino)acetate, shown below.

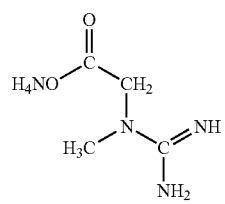

Finally, in a dry 2-necked, round bottomed flask, fixed with a separatory funnel, containing 17.93 g (60 mmol) of the prepared (9Z,12Z)-octadeca-9,12-dienoyl chloride, and side arm water condenser fixed with a dry receiving flask, is placed 10.66 g (72 mmol) of ammonium 2-(1-methylguanidino)acetate. The round bottomed flask is placed in an ice bath and the (9Z,12Z)-octadeca-9,12-dienoyl chloride is added drop wise. After addition is completed the mixture is shaken and the ice bath is replaced by a heating mantle. The flask is then heated until no more solution is dropping into the receiving flask. This crude distillate is then further fractionally distilled to yield 2-(1-methylguanidino)acetic(9Z,12Z)-octadeca-9, 12-dienoic anhydride.

Thus while not wishing to be bound by theory, it is understood that reacting a creatine or derivative thereof with a fatty acid or derivative thereof to form an anhydride can be used enhance the bioavailability of the creatine or derivative thereof by improving stability of the creatine moiety in terms of resistance to hydrolysis in the stomach and blood and by increasing solubility and absorption. Furthermore, it is understood that, dependent upon the specific fatty acid, for example, saturated fatty acids form straight chains allowing mammals to store chemical energy densely, or derivative thereof employed in the foregoing synthesis, additional fatty acid-specific benefits, separate from the creatine substituent, will be conferred.

EXTENSIONS AND ALTERNATIVES

In the foregoing specification, the invention has been described with a specific embodiment thereof; however, it will be evident that various modifications and changes may be made thereto without departing from the broader spirit and scope of the invention.

What is claimed is:

1. A method for producing creatine fatty acids comprising at least the steps of:
   mixing an excess of a thionyl halide with a fatty acid to form an acyl halide;
   neutralizing the carboxylic acid of a creatine with an inorganic base to form a creatine salt;
   said acyl halide then being reacted with the creatine salt; and
   isolating the resulting creatine fatty acid.

2. The method of claim 1 wherein the halide of the thionyl halide is selected from the group consisting of fluorine, chlorine, bromine, and iodine.

3. The method of claim 1 wherein the acyl halide is produced at temperatures from between about 35° C. to about 50° C.

4. The method of claim 1 wherein the inorganic base is selected group consisting of sodium hydroxide, potassium hydroxide, lithium hydroxide, ammonium hydroxide, sodium carbonate.

5. The method of claim 1 wherein the creatine fatty acid is isolated by distillation.

6. The method of claim 1 wherein the creatine fatty acid has the general structure of:

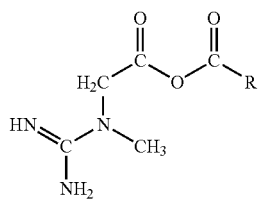
wherein R is selected from the group consisting of alkanes and alkenes;
said alkanes and alkenes having from 3 to 21 carbons.
* * * * *